United States Patent
Watanabe (10) Patent No.: US 10,267,681 B2
(45) Date of Patent: Apr. 23, 2019

(54) QUANTUM YIELD CALCULATION METHOD, SPECTROPHOTOFLUOROMETER, AND QUANTUM YIELD CALCULATION PROGRAM

(71) Applicant: SHIMADZU CORPORATION, Nakagyo-Ku, Kyoto-Shi, Kyoto (JP)

(72) Inventor: Yasuyuki Watanabe, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 15/951,885

(22) Filed: Apr. 12, 2018

(65) Prior Publication Data
US 2018/0306645 A1 Oct. 25, 2018

(30) Foreign Application Priority Data
Apr. 19, 2017 (JP) .................. 2017-083150

(51) Int. Cl.
*G01J 3/44* (2006.01)
*G01J 3/02* (2006.01)
(Continued)

(52) U.S. Cl.
CPC ............. *G01J 3/4406* (2013.01); *G01J 3/027* (2013.01); *G01J 3/0254* (2013.01); *G01J 3/18* (2013.01);
(Continued)

(58) Field of Classification Search
CPC .. G01J 3/18; G01J 3/4406; G01N 2021/6419; G01N 2021/6421; G01N 21/31; G01N 21/645
See application file for complete search history.

(56) References Cited

U.S. PATENT DOCUMENTS

| 2011/0226961 A1 | 9/2011 | Osawa et al. |
| 2016/0090322 A1* | 3/2016 | Okamoto .................. C03C 4/12 359/342 |

(Continued)

FOREIGN PATENT DOCUMENTS

| JP | 3 287775 | 6/2002 |
| JP | 2016151426 | 8/2016 |

OTHER PUBLICATIONS

EP 18167843.4, Extended European Search Report dated Sep. 14, 2018, 8 pags—English.

*Primary Examiner* — Mark R Gaworecki
(74) *Attorney, Agent, or Firm* — Andrew F. Young, Esq.; Lackenbach Siegel, LLP (57) ABSTRACT

A quantum yield calculation method uses a quantum yield calculation program for a spectrophotofluorometer. When a quantum yield is calculated using a spectrophotofluorometer 1, a calibration processing unit executes the processing to calibrate a photon number A2 that is a photon number of the fluorescence in a blank measurement state based on a photon number A1 that is the photon number of an excitation light in the blank measurement state and a photon number B1 that is the photon number of an excitation light in the sample measurement state. A quantum yield calculation processing unit calculates a first quantum yield based on a background photon number A2' after a calibration in addition to the photon number A1 of the excitation light in the blank measurement state and the photon number B2 of the fluorescence in the sample measurement state.

9 Claims, 8 Drawing Sheets

(51) Int. Cl.
    *G01J 3/28*         (2006.01)
    *G01J 3/18*         (2006.01)
    *G01N 21/64*       (2006.01)
    *G01N 21/31*       (2006.01)
    *G01J 3/12*         (2006.01)

(52) U.S. Cl.
    CPC ............... *G01J 3/28* (2013.01); *G01N 21/31* (2013.01); *G01N 21/645* (2013.01); *G01J 2003/1213* (2013.01); *G01N 2021/6417* (2013.01); *G01N 2021/6419* (2013.01); *G01N 2021/6421* (2013.01); *G01N 2201/065* (2013.01)

(56) References Cited

U.S. PATENT DOCUMENTS

| | | | |
|---|---|---|---|
| 2016/0115379 A1* | 4/2016 | Kida | C09K 11/02 257/98 |
| 2016/0152515 A1* | 6/2016 | Okamoto | C03C 3/325 252/301.4 F |

\* cited by examiner

QUANTUM YIELD CALCULATION METHOD, SPECTROPHOTOFLUOROMETER, AND QUANTUM YIELD CALCULATION PROGRAM

CROSS REFERENCE TO RELATED APPLICATIONS

This application relates to, and claims priority from, JP Ser. No.: JP2017-083150 filed Apr. 19, 2017, the entire contents of which are incorporated herein by reference.

FIGURE SELECTED FOR PUBLICATION

FIG. 3

BACKGROUND OF THE INVENTION

Field of the Invention

The present invention relates to a spectrophotofluorometer that acquires a spectrum by irradiating an excitation light to be incident into the inside of the integrating sphere in which a measurement position, at which a sample is in-place, is formed and detecting the light emitted from the inside of the integrating sphere. Further, the present invention relates to a quantum yield calculation method that calculates a quantum yield based on such spectrum and a quantum yield calculation program therefor.

Description of the Related Art

Conventionally, it has been studied in a photoreactive molecule that reacts to a light having a specific wavelength component to attain a target function.

The photoreactive molecule is normally in the energetically stable ground state and absorbs the light-energy to be in the excited state when an excitation light having the specific wavelength component is irradiated thereto. Then after, the photoreactive molecule emits a fluorescence or a phosphorescence and returns (drops) to the original-stable ground state. Now, for example, a ratio between the irradiated or absorbed photon number of the light and the photon number of the emitted light represents a quantum yield.

Such quantum yield is calculated by using, for example, the spectrophotofluorometer having the integrating sphere (e.g., the Patent Document 1 below).

Specifically, when the quantum yield is calculated using the spectrophotofluorometer, an excitation light is first irradiated to be incident into the integrating sphere without a sample at the measurement position in the integrating sphere. Then, the spectrum is obtained by detecting the light emitted from the integrating sphere. Next, the spectrum is obtained using the same with a sample at the measurement position in the integrating sphere. Then, each photon number of the lights emitted from the integrating sphere is calculated under each state with the sample and without the sample based on the obtained spectra. In addition, the quantum yield is calculated based on such photon numbers.

RELATED PRIOR ART DOCUMENTS

Patent Document
Patent Document 1: JP Patent Published 2016-151426 A1

ASPECTS AND SUMMARY OF THE INVENTION

Objects to be Solved

According to the conventional method as set forth above, one drawback is a possible drop of the accuracy of the calculated quantum yield. Specifically, relative to the conventional method, the light emitted from the integrating sphere may contain so-called a background component (i.e., stray light component) such as a fluorescence emerged by collision of the light against the wall of the integrating sphere. Therefore, the accuracy of the quantum yield may drop due to such background component. In addition, even when the quantum yield is calculated following the calculation of the background component, if the accuracy level of calculation of the background component is inferior, the accuracy of the quantum yield drops.

Considering such circumstance, the purpose of the present invention is to provide a quantum yield calculation method that can calculate a quantum yield with high-accuracy, a spectrophotofluorometer therefor and a quantum yield calculation program therefor.

Means for Solving the Problem (1) According to the aspect of the present invention, the quantum yield calculation method calculates the quantum yield based on the spectrum obtained by irradiating the excitation light to be incident to the inside of the integrating sphere and detecting the light emitted from the inside of the integrating sphere, in which a measurement position, at which a sample is in-place, is formed therein. The quantum yield calculation method comprises a step of measuring a blank (blank measurement step), a step of measuring a sample (sample measurement step), a step of calibrating (calibration step) and a step of calculating the quantum yield (quantum yield calculation step). The blank measurement step calculates a first photon number that is the photon number of the excitation light incident into the integrating sphere, based on the spectrum obtained by irradiating the excitation light under the blank state in which only base material is placed or only solvent therein with no sample at the measurement position, and in addition, calculates a second photon number that is a photon number of the light in the different wavelength range from the wavelength range of the excitation light. The sample measurement step calculates a third photon number that is the photon number of the excitation light incident to the integrating sphere, based on the spectrum obtained by irradiating the excitation light under the sample measurement state in which the sample is placed at the measurement position, and in addition, calculates a fourth photon number that is a photon number of the light in the specific wavelength range. The calibration step calculates a fifth photon number by calibrating the second photon number based on the first photon number and the third photon number. The quantum yield calculation step calculates a quantum yield based on the first photon number, the fourth photon number and the fifth photon number.

According to such method, the calibration step calculates the fifth photon number by calibrating the second photon number that is a photon number of the light in the specific wavelength range relative to the blank measurement state based on the first photon number that is the photon number of the excitation light relative to the blank measurement and the third photon number that is the photon number of the excitation light relative to the sample measurement state.

Therefore, the photon number of the light in the specific wavelength range in the blank measurement state can be highly accurately calculated by such calibration.

In addition, the quantum yield calculation step calculates the quantum yield based on the fifth photon number obtained by calibrating the second photon number that is a photon number of the light in the specific wavelength range relative to the blank measurement state in addition to the first photon number that is the photon number of the excitation light in the blank measurement state and the fourth photon number that is the photon number of the light in the specific wavelength range in the sample measurement state.

Specifically, the quantum yield calculation step calculates the quantum yield using the fifth photon number that is well accurately calculated by such calibration.

In such way, according to the method set forth above, the photon number of the light in the specific wavelength range in the blank measurement state is more accurately calculated by calibration, and the quantum yield is calculated using such photon number.

Therefore, the quantum yield can be well accurately calculated.

(2) The quantum yield calculation step can calculate a ratio between the photon number of excitation light incident into the integrating sphere and the photon number of the light emerged from the sample as an outside quantum yield based on the first photon number, the fourth photon number and the fifth photon number.

Therefore, the outside quantum yield can be well accurately calculated.

(3) In addition, the quantum yield calculation step can calculate a ratio between the photon number of excitation light absorbed by the sample and the photon number of the light emerged from the sample as an inside quantum yield based on the first photon number, the third photon number, the fourth photon number and the fifth photon number as the inside quantum yield.

According to such method, the inside quantum yield can be well accurately calculated.

(4) In addition, relative to the blank measurement step, the second photon number and the first photon number can be calculated based on each spectrum obtained in the state in which an optical filter, of which the transmittance in the wavelength range of the excitation light is reduced, is placed on the light-path and in the state, in which no optical filter is placed on the light-path. Relative to the sample measurement step, the fourth photon number and the third photon number can be calculated based on each spectrum obtained in the state in which an optical filter is placed on the light-path and in the state in which no optical filter is placed on the light-path.

According to such method, the second photon number is calculated based on the spectrum obtained in the blank measurement state and in the state in which the optical filter is placed on the light-path. The fourth photon number is calculated based on the spectrum obtained in the sample measurement state and in the state in which the optical filter is placed on the light-path. Therefore, when the second photon number and the fourth photon number are respectively calculated, a noise due to the light in the wavelength range of the excitation light can be removed.

As results, the quantum yield can be further well accurately calculated.

(5) The spectrophotofluorometer, according to the aspect of the present invention, acquires the spectrum by irradiating the excitation light to be incident into the inside of the integrating sphere; in which a measurement position, at which a sample is in-place, is formed; and by detecting the light emitted from the inside of the integrating sphere. The spectrophotofluorometer comprises a blank measurement processing unit, a sample measurement processing unit, a calibration processing unit and a quantum yield calculation processing unit. The blank measurement processing unit calculates the first photon number that is the photon number of the excitation light incident into the integrating sphere and the second photon number that is a photon number of the light in the different wavelength range from the wavelength range of the excitation light based on the spectrum obtained by irradiating the excitation light into the integrating sphere in the blank measurement state in which no sample is placed at the measurement position. The sample measurement processing unit calculates the third photon number that is the photon number of the excitation light that is not absorbed by the sample, based on the spectrum obtained by irradiating the excitation light to be incident into the integrating sphere under the sample measurement state in which the sample is placed at the measurement position, and in addition, calculates the fourth photon number that is the photon number of the light in the specific wavelength range. The calibration processing unit calculates the fifth photon number by calibrating the second photon number based on the first photon number and the third photon number. The quantum yield calculation processing unit calculates a quantum yield based on the first photon number, the fourth photon number and the fifth photon number.

(6) In addition, the quantum yield calculation processing unit can calculate the ratio between the photon number of excitation light incident into the integrating sphere and the photon number of the light emerged from the sample as an outside quantum yield based on the first photon number, the fourth photon number and the fifth photon number.

(7) In addition, the quantum yield calculation processing unit can calculate a ratio between the photon number of excitation light absorbed by the sample and the photon number of the light emerged from the sample as an inside quantum yield based on the first photon number, the third photon number, the fourth photon number and the fifth photon number.

(8) In addition, the blank measurement processing unit can calculate the second photon number and the first photon number based on each spectrum obtained in the state in which an optical filter, of which the transmittance in the wavelength range of the excitation light is reduced, is placed on the light-path and in the state, in which no optical filter is placed on the light-path. The sample measurement processing unit can calculate the fourth photon number and the third photon number based on each spectrum obtained in the state in which an optical filter is installed on the light-path and in the state in which no optical filter is installed on the light-path.

(9) According to the aspect of the present invention, the quantum yield calculation program calculates the quantum yield based on the spectrum obtained by irradiating the excitation light to be incident into the inside of the integrating sphere and detecting the light emitted from the inside of the integrating sphere, in which a measurement position, at which a sample is in-place, is formed therein. The quantum yield calculation program executes the step of measuring the blank, the step of measuring a sample, the step of calibrating and the step of calculating the quantum yield using a computer. The blank measurement step calculates the first photon number that is the photon number of the excitation light incident into the integrating sphere and the second photon number that is a photon number of the light in the different wavelength range from the wavelength range of the excitation light based on the spectrum obtained by irradiating the excitation light into the integrating sphere in the blank measurement state in which no sample is placed at the measurement position. The sample measurement step calculates a third photon number that is the photon number of the excitation light incident to the integrating sphere, based on the spectrum obtained by irradiating the excitation light under the sample measurement state in which the sample is placed at the measurement position, and in addition, calculates a fourth photon number that is a photon number of the light in the specific wavelength range. The calibration step calculates a fifth photon number by calibrating the second photon number based on the first photon number and the third photon number. The step of calculating a quantum yield calculates a quantum yield based on the first photon number, the fourth photon number and the fifth photon number.

Effect of the Invention

According to the aspect of the present invention, the photon number of the light in the specific wavelength range relative to the blank measurement state is more accurately calculated by calibration, and the quantum yield is calculated using such photon number. Therefore, the quantum yield can be well accurately calculated.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

It will be further understood by those of skill in the art that the apparatus and devices computing devices and storage drives that retain memory storing programs, and related computational elements therefore, without limitation, may optionally including the sub components such as operational structures, circuits, communication pathways, and memory elements and processing elements, control elements of all kinds, display circuits and display systems and elements, any necessary driving elements, inputs, sensors, detectors, memory modules, processors and any combinations of these structures etc. as will be understood by those of skill in the art as also being identified as or capable of operating the algorithm steps, calculation steps, and systems, and programs and devices and subcomponents noted herein and structures that accomplish the steps and functions without restrictive language or label requirements since those of skill in the art are well versed in related computing, calculation, processing, and related technologies of quantum yield calculation, spectrophotofluorometers, and calculation programs, devices computers and operational controls and technologies of spectrophotofluorometer devices and all their sub components, including various circuits, circuit components (resistors, capacitors, transistors, etc.) and combinations of circuits without departing from the scope and spirit of the present invention.

As used herein, a processing unit or detection or display element comprises any necessary functional and structural requirements for receiving data, and for outputting data in tangible form (e.g. calculation data, processed data, calculation data, measurement data, printing or imagery displaying on an electronic screen), a memory for storing any data as well as required code, and a processor or microprocessor for executing code wherein the computer code resident in the memory will physically cause said processor/microprocessor to read-in data via said input device, process said data within said microprocessor and output said processed data via said output device.

1. Configuration of a Spectrophotofluorometer

Figure 1:
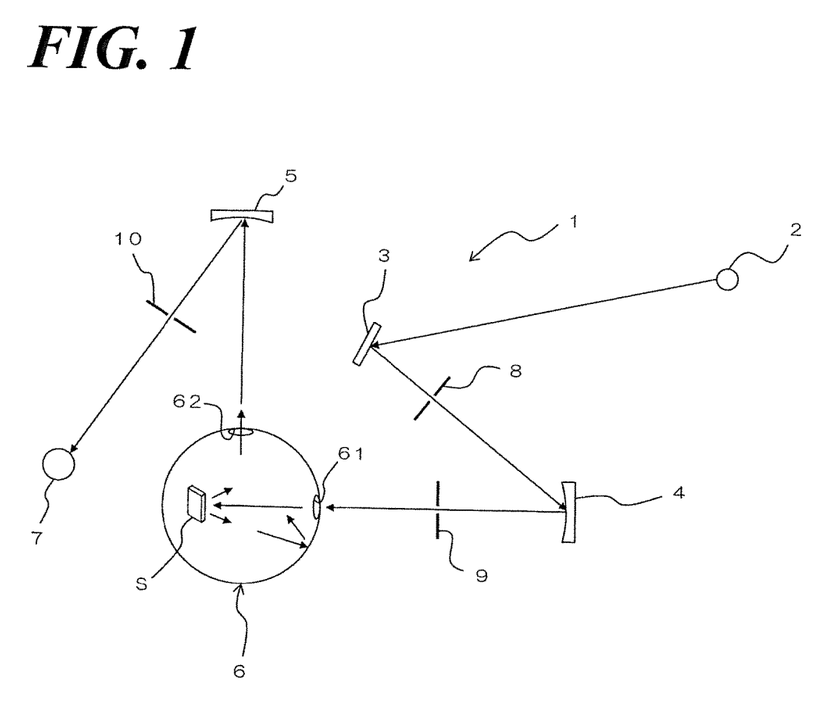
FIG. 1 is a schematic diagram illustrating an example of the structure of a spectrophotofluorometer according to the aspect of the Embodiment 1 of the present invention.

FIG. 1 is a schematic diagram illustrating an example of the structure of a spectrophotofluorometer 1 according to the aspect of the Embodiment 1 of the present invention.

The spectrophotofluorometer 1 comprises a light source 2; a mirror 3; gratings 4, 5; an integrating sphere 6, a detection element 7 and slits 8, 9, 10.

The light source 2 is e.g., a xenon lamp. The light source 2 emits a white-light as an excitation light.

The mirror 3 is in-place to be away from the light source 2 in some distance.

The gratings 4, 5 are concave-gratings. The gratings 4, 5 are respectively in-place in the periphery of the integrating sphere and to be away from each other. Each of the gratings 4, 5 is rotatable. Each of the gratings 4, 5 rotates, so that each grating disperses the incident light and emits the light having an arbitrary wavelength.

The integrating sphere 6 is formed to be hollow and spherical. The integrating sphere 6 has an incident entrance 61 and an emittance exit 62. The incident entrance 61 of the integrating sphere 6 is away from the grating 4 and facing thereto. The emittance exit 62 of the integrating sphere 6 is away from the grating 5 and facing thereto. The measurement position is formed in the integrating sphere 6, and a sample S is in-place at the measurement position.

The detection element 7 is in-place to be away from the grating 5 in some distance.

The slit 8 is in-place between the mirror 3 and the grating 4. The slit 9 is in-place between the mirror 4 and the integrating sphere 6. The slit 10 is in-place between the grating 5 and the detection element 7.

When the spectrum is acquired using the spectrophotofluorometer 1, the light source 2 first irradiates white-light (excitation light) toward the mirror 3. The white-light that the light source 2 irradiates is reflected at the mirror 3 and is incident to the grating 4 following passing the slit 8. And the grating 4 disperses the incident light to the excitation light having a specific wavelength. The dispersed excitation light is incident into the inside of the integrating sphere 6 via the incident entrance 61 and is irradiated to the sample S following passing the slit 9.

When the excitation light is irradiated to the sample S, a part of the excitation light is absorbed by molecules of the sample S. And the molecule of the sample S transits from the ground state to the excited state having a high-energy level. Then, the molecule in the excited state drops to the ground state by deactivation along with light radiation. Now, the molecule of the sample S emits a fluorescence.

Then lights containing the fluorescence is emitted from the emittance exit 62 of the integrating sphere 6. The light emitted from the integrating sphere 6 is dispersed by the grating 5. Now, the grating 5 rotates, so that the light dispersed every wavelength is incident continuously to the detection element 7. The detection element 7 outputs a detection signal corresponding to the light intensity every time when the light dispersed every wavelength is incident. Then, the spectrophotofluorometer 1 generates a spectrum based on the detection signal from the detection element 7.

The spectrophotofluorometer 1 can calculates the quantum yield using the spectrum acquired in such way. Specifically, the spectrum is generated by that the exciting light is incident into the integrating sphere 6 and detecting the light emitted from the integrating sphere 6 by the detection element 7, as well as set forth above, in both states in which the sample S is not in-place in the integrating sphere 6 and sample S is in-place in the integrating sphere 6 (the above state). In addition, the quantum yield is calculated based on such spectra. The spectrophotofluorometer has the below configuration and uses the below method so that the quantum yield can be more accurately calculated.

Figure 2:
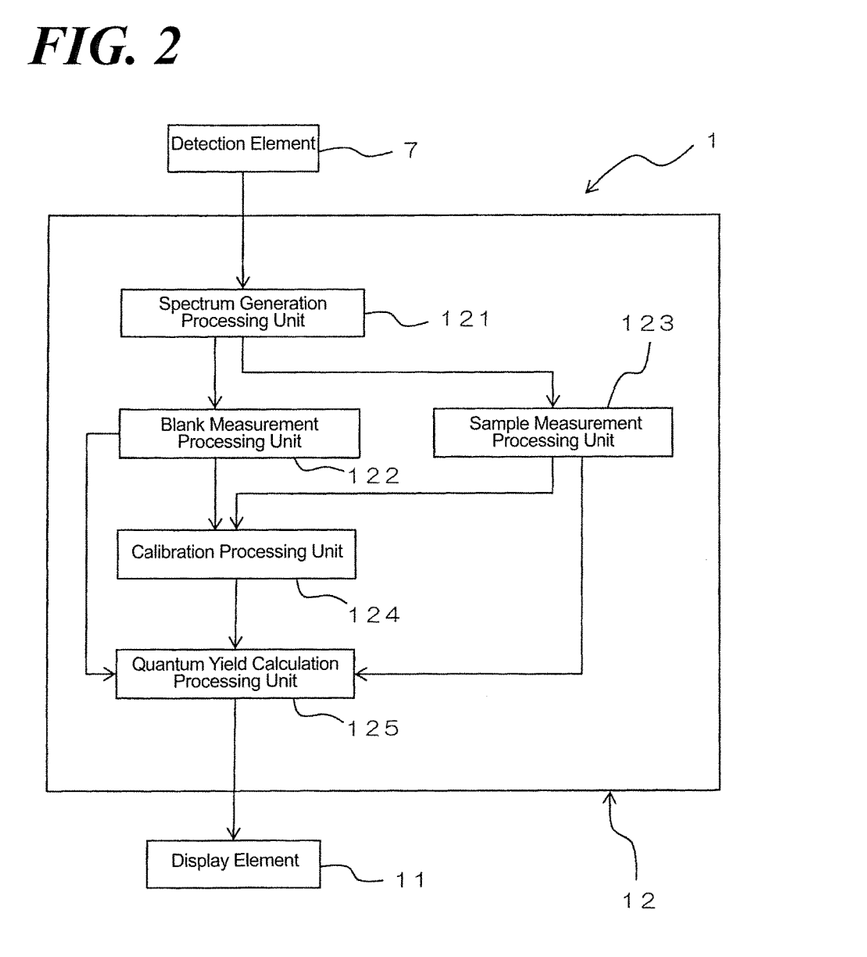
FIG. 2 is a block diagram illustrating the control element of the spectrophotofluorometer in FIG. 1 and the electrical configuration of the peripheral members thereof.

2. Control Element and an Electrical Configuration of the Peripheral Members Thereof FIG. 2 is a block diagram illustrating the control element of the spectrophotofluorometer 1 and the electrical configuration of the peripheral members thereof. The spectrophotofluorometer 1 comprises a display element 11 and the control element 12 as an electrical component in addition to the detection element 7. The display element 11 comprises e.g., a liquid crystal display.

The control element 12 comprises e.g., a CPU (central processing unit which is a computing device). The control element 12 electrically connects the detection element 7, the display element 11 and so forth. When the CPU executes programs (stored in memory), the control element 12 is operative as the spectrum generation processing unit 121 (also a computing processing unit), the blank measurement processing unit 122, the sample measurement processing unit 123, the calibration processing unit 124 and the quantum yield calculation processing unit 125 and so forth to operate as discussed and to conduct the method and algorithm processing steps and processing calculations as noted herein. It is understood that those of skill in the art are very highly skilled in science, engineering, physic, and programming at a minimum at a graduate level and therefore fully understand the related details which are not necessary to relate here.

The spectrum generation processing unit 121 executes the processing to generate the spectrum based on the detection signal from the detection element 7. Specifically, the spectrum generation processing unit 121 generates the spectrum (blank spectrum) based on the detection signal from the detection element 7 in the state (blank measurement state) in which the sample S is not at the measurement position in the integrating sphere 6. In addition, the spectrum generation processing unit 121 generates the spectrum (sample spectrum) based on the detection signal from the detection element 7 in the state (sample measurement state) in which the sample is at the measurement position in the integrating sphere 6.

The blank measurement processing unit 122 executes the processing to calculate the photon number (first photon number) that is the photon number of the excitation light incident into the integrating sphere 6 and the photon number (second photon number) that is a photon number of the fluorescence (light in the different specific wavelength range from the wavelength range of the excitation light) based on the spectrum (blank spectrum) that the spectrum generation processing unit 121 generates.

The sample measurement processing unit 123 executes the processing to calculate the photon number (third photon number) that is the photon number of the excitation light not-absorbed by the sample S and the photon number (fourth photon number) that is a photon number of the fluorescence (light in the different specific wavelength range from the wavelength range of the excitation light) based on the spectrum (sample spectrum) that the spectrum generation processing unit 121 generates.

The calibration processing unit 124 executes the processing to calibrate the photon number (fourth photon number) of the fluorescence calculated by the sample measurement processing unit 123 based on the photon number (first photon number) of the excitation light that the blank measurement processing unit 122 calculates and the photon number (third photon number) of the excitation light that the sample measurement processing unit 123 calculates.

The quantum yield calculation processing unit 125 executes the processing to calculate the quantum yield based on the photon number (first photon number) of the excitation light that the blank measurement processing unit 122 calculates, the photon number (fourth photon number) of the fluorescence that the sample measurement processing unit 123 calculates, and the photon number (fifth photon number) that the calibration processing unit 124 calibrates. The quantum yield calculation processing unit 125 calculates, as set forth later, the outside quantum yield or the inside quantum yield as the quantum yield.

3. Control Operation by the Control Element

Figure 3:
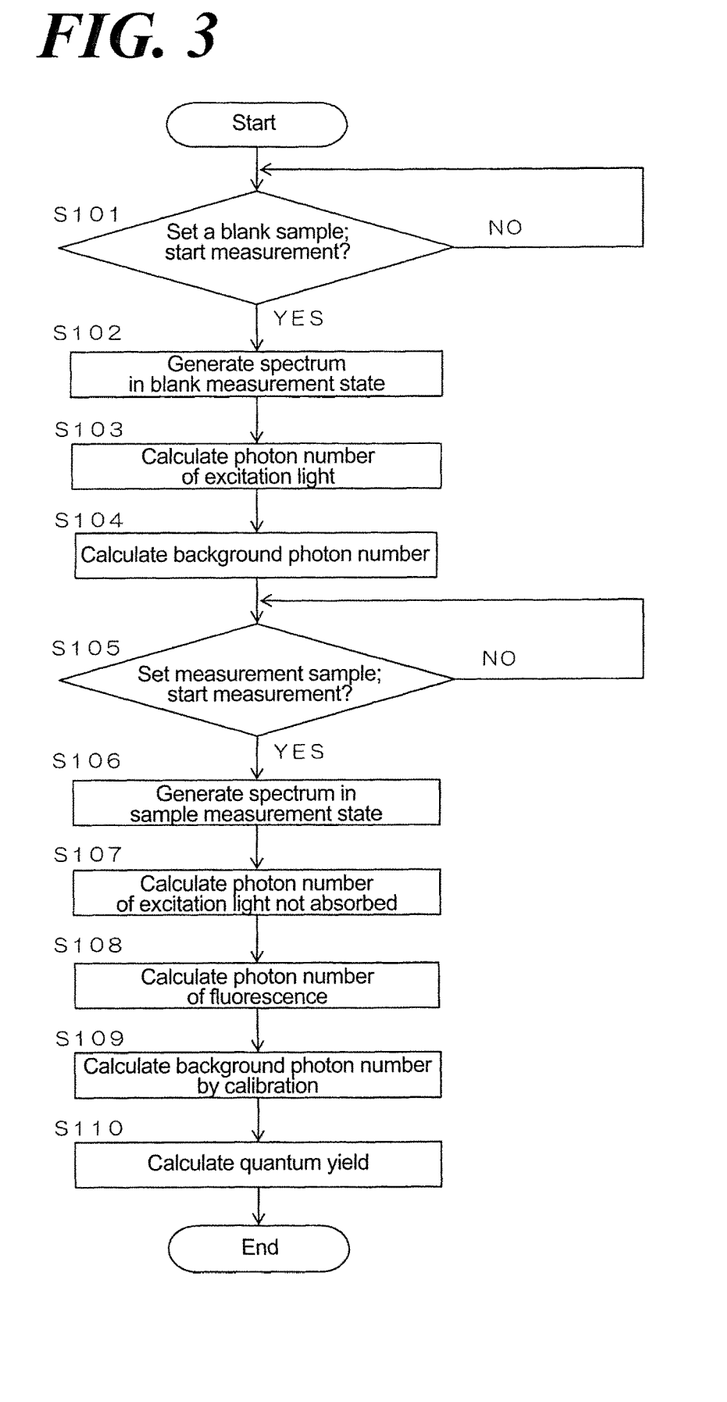
FIG. 3 is a flow-chart illustrating an example of the control operations of the spectrophotofluorometer in FIG. 1.
Figure 4:
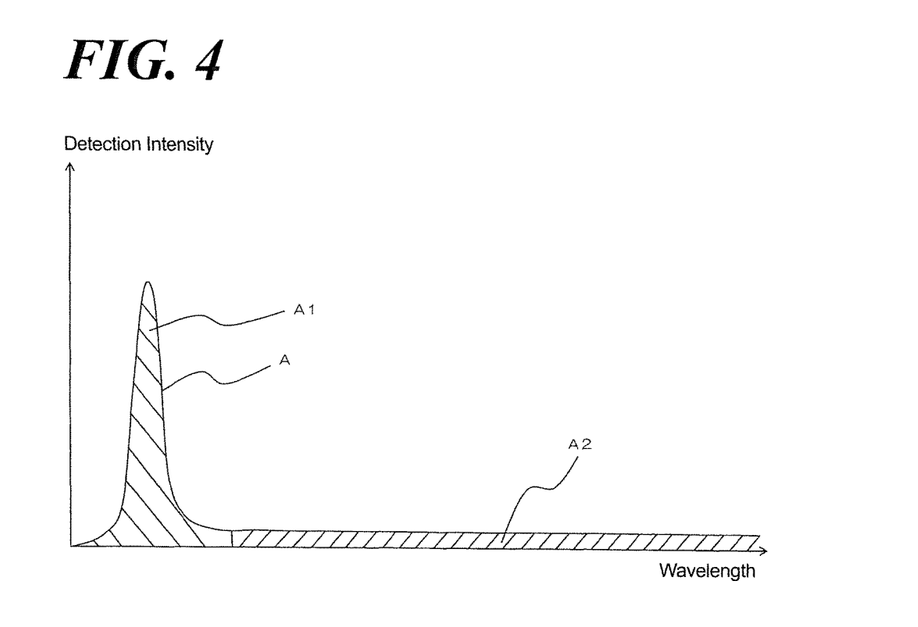
FIG. 4 is a spectrum generated using the spectrophotofluorometer, and the spectrum is obtained by allowing the excitation light to be incident into the integrating sphere in the blank measurement state.
Figure 5:
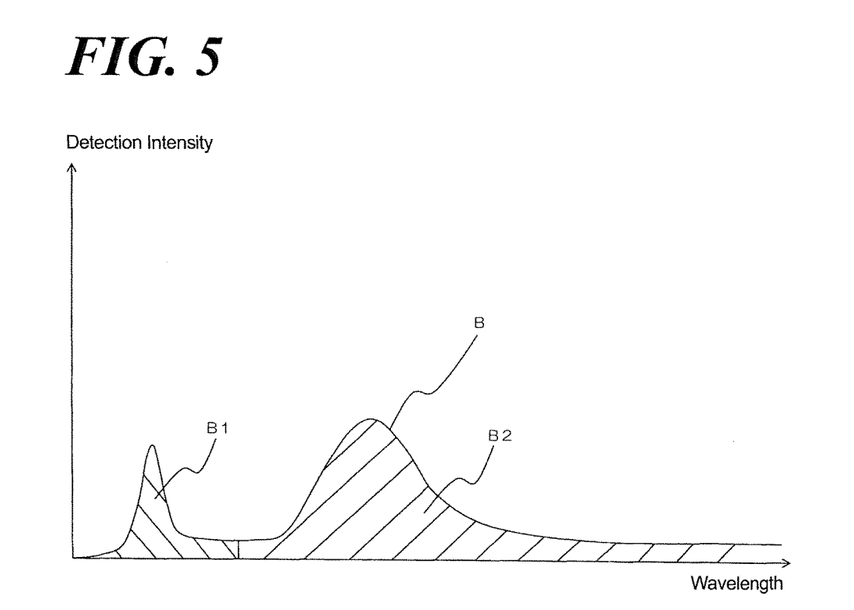
FIG. 5 is a spectrum generated using the spectrophotofluorometer, and the spectrum is obtained by allowing the excitation light to be incident into the integrating sphere in the blank measurement state.
Figure 6:
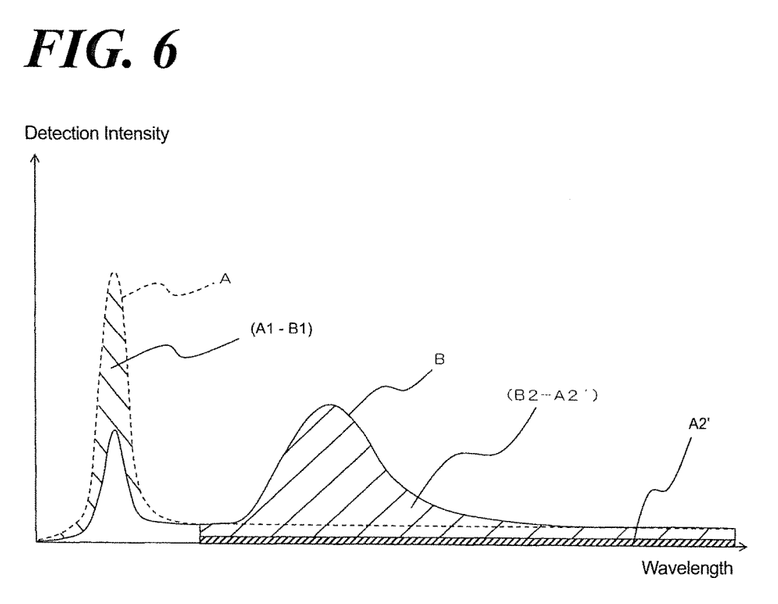
FIG. 6 is an explanatory view illustrating the photon number that is applied when the quantum yield is acquired.

FIG. 3 is a flow-chart illustrating an example of the control operations of the control element 12. FIG. 4 is a spectrum generated using the spectrophotofluorometer 1, and the spectrum is obtained by allowing the excitation light to be incident into the integrating sphere 6 in the blank measurement state. FIG. 5 is a spectrum generated using the spectrophotofluorometer 1, and the spectrum is obtained by allowing the excitation light to be incident into the integrating sphere 6 in the sample measurement state. FIG. 6 is an explanatory view illustrating the photon number that is applied when the quantum yield is acquired. In FIG. 4-FIG. 6, the horizontal axis denotes a wavelength and the vertical axis denotes a detection intensity. Hereafter, referring to FIG. 3-FIG. 6, the inventor sets forth the control operation of the control element 12.

When the quantum yield of a sample is acquired using the spectrophotofluorometer 1, the user starts the operation of the spectrophotofluorometer 1 by operating the operation element, not shown in FIG., in the state (blank measurement state) in which no sample S is placed in the integrating sphere 6.

When the user carries out an input operation through the operation element to start the action (Yes in the step S101), the light source 2 radiates the excitation light and such excitation light is incident into the integrating sphere 6. And the light emitted from the integrating sphere 6 is detected by the detecting element 7. Specifically, the spectrum generation processing unit 121 generates the spectrum (blank spectrum) based on the detection signal from the detection element 7 in the blank measurement state (step S102). Referring to FIG. 4, the spectrum (blank spectrum) that the spectrum generation processing unit 121 generates is indicated as A. Referring to the spectrum A, the excitation light appears in the short-wavelength side and the fluorescence appears in the long-wavelength side.

And the blank measurement processing unit 122 calculates the photon number A1 of the excitation light from the spectrum A (blank spectrum A) (step S103). The photon number A1 corresponds to the area of the spectrum A in the wavelength range of the excitation light. The photon number is one example of the first photon number A1.

And the blank measurement processing unit 122 calculates the photon number A2 of the fluorescence from the spectrum A (blank spectrum A) (step S104: blank measurement step). The photon number A2 corresponds to the area of the spectrum A in the wavelength range of the fluorescence. The photon number A2 is so-called background component (background photon number) that is the fluorescence component and so forth emerged due to e.g., the property of the inner wall material in the integrating sphere 6. The photon number A2 is one example of the second photon number. Then, the user starts the operation of the spectrophotofluorometer 1 by re-operating the operation element following placement of the sample S at the measurement position in the integrating sphere 6.

When the user carries out an input operation through the operation element to start the action (Yes in the step S105), the light source 2 radiates the excitation light and such excitation light is incident into the integrating sphere 6. And the light emitted from the integrating sphere 6 is detected by the detecting element 7. The spectrum generation processing unit 121 generates the spectrum (sample spectrum) based on the detection signal from the detection element 7 in the sample measurement state (step S106). Referring to FIG. 5, the spectrum (sample spectrum) that the spectrum generation processing unit 121 generates is indicated as B. Referring to the spectrum B, the excitation light appears in the short-wavelength side and the fluorescence appears in the long-wavelength side.

And the sample measurement processing unit 123 calculates the photon number B1 of the excitation light from the spectrum B (sample spectrum B) (step S107). The photon number B1 corresponds to the area of the spectrum B in the wavelength range of the excitation light. The photon number B1 is the photon number of the excitation light that the sample S does not absorb. The photon number B1 is one example of the third photon number.

In addition, the sample measurement processing unit 123 calculates the photon number B2 of the fluorescence from the spectrum B (sample spectrum B) (step S108: sample measurement step). The photon number B2 corresponds to the area of the spectrum B in the wavelength range of the fluorescence. The photon number B2 includes the fluorescence emerged from the sample S and the fluorescence as the background component. The photon number B2 is one example of the fourth photon number.

And the calibration processing unit 124 executes the processing to calibrate the photon number A2 based on the photon number A1 and the photon number B1 (step S109: calibration step). Specifically, the calibration processing unit 124 calibrate the photon number A2 according to the following formula (1).

$$A2'=(B1/A1) \times A2 \qquad (1)$$

The above formula (1) provides the ratio (B1/A1) between the photon number A1 of the excitation light in the blank measurement state and the photon number B1 of the excitation light in the sample measurement state and expresses that the photon number A2 is calibrated by multiplying the provided ratio to the photon number A2 that is the background component (background photon number) in the blank measurement state. A2' is the photon number (background photon number after calibration) obtained after calibrating the A2 and one example of the fifth photon number.

In such way, the calibration processing unit 124 calculates the ratio between the photon number A1 (radiation photon number) of the excitation light in the blank measurement state and the photon number B1 of the excitation light that is not absorbed by the sample S and collides with the inner wall of the integrating sphere 6 and calibrates the photon number A2 in accordance with such ratio.

In addition, the quantum yield calculation processing unit 125 calculates a quantum yield based on the photon number A1, the photon number B2 and the photon number A2' (step S110: quantum yield calculation step). Now, the quantum yield calculation processing unit 125 calculates the outside quantum yield or the inside quantum yield as the quantum yield. Specifically, the quantum yield calculation processing unit 125 executes the processing to calculate the quantum yield according to the following formula (2) when the outside quantum yield is calculated.

$$Y1=(B2-A2')/A1 \qquad (2)$$

In the above formula (2), Y1 denotes the outside quantum yield. The above formula (2) provides the value obtained by subtracting the background photon number A2' after calibration from the photon number B2 of the fluorescence in the sample measurement state, i.e., the photon number (B2–A2') of the fluorescence emitted only from the sample S and expresses that the ratio between the photon number A1 of the excitation light (photon number A1 of the excitation light to be incident into the integrating sphere 6) in the blank measurement state and the calculated photon number (B2–A2') is calculated as the outside quantum yield (Y1). Referring to FIG. 6, the fluorescence photon number (B2–A2') emerged only from the sample S and the background photon number A2' after calibration are indicated by the diagonal lines.

In addition, the quantum yield calculation processing unit 125 executes the processing to calculate the quantum yield according to the following formula (3) when the inside quantum yield is calculated. Now, the quantum yield calculation processing unit 125 calculates the inside quantum yield based on the photon number B1 in addition to the photon number A1, the photon number B2 and the photon number A2'.

$$Y2=(B2-A2')/(A1-B1) \quad (3)$$

In the above formula (3), Y2 denotes the inside quantum yield. The above formula (3) provides the value obtained by subtracting the background photon number A2' after calibration from the photon number B2 of the fluorescence in the sample measurement state, i.e., the photon number (B2–A2') only from the sample S and expresses that the ratio between the photon number (A1–B1) of the excitation light absorbed by the sample S and the calculated photon number (B2–A2') is calculated as the inside quantum yield (Y2). Referring to FIG. 6, the photon number (A1–B1) is the photon number of the excitation light absorbed by the sample S is indicated by the diagonal lines. And, the quantum yield (outside quantum yield or inside quantum yield) that the quantum yield calculation processing unit 125 calculates is displayed on the display unit 11.

4. Action and Effect (1) According to the aspect of the present Embodiment, when the quantum yield is calculated using the spectrophotofluorometer 1, the calibration processing unit 124 executes the processing to calibrate the photon number A2 (second photon number) that is a photon number of the fluorescence in the blank measurement state based on the photon number A1 (first photon number) that is the photon number of the excitation light in the blank measurement state and the photon number B1 (third photon number) that is the photon number of the excitation light not-absorbed by the sample S in the sample measurement state (step S109: calibration step).

Specifically, the calibration processing unit 124 calculates the ratio between the photon number A1 (radiation photon number) of the excitation light in the blank measurement state and the photon number B1 of the excitation light that is not absorbed by the sample S and collides with the inner wall of the integrating sphere 6, and calibrates the photon number A2, which is the background component (background photon number) in the blank measurement state, in accordance with such ratio. Therefore, the photon number A2 is calibrated, so that the background photon number A2' after the calibration can be calculated more accurately.

In addition, the quantum yield calculation processing unit 125 calculates the quantum yield based on the background photon number A2' (fifth photon number) after the calibration in addition to the photon number A1 (first photon number) of the excitation light in the blank measurement state and the photon number B2 (fourth photon number) of the fluorescence in the sample measurement state (step S110: quantum yield calculation step). Specifically, the quantum yield calculation processing unit 125 calculates the quantum yield using the background photon number A2' after the calibration (fifth photon number) that is well accurately calculated by calibration. Therefore, the quantum yield can be well accurately calculated.

(2) In addition, according to the aspect of the present Embodiment, the quantum yield calculation processing unit 125 calculates the outside quantum yield based on the photon number A1, the photon number B2 and the photon number A2'. Specifically, the quantum yield calculation processing unit 125 calculates the ratio between the photon number A1 of the excitation light in the blank measurement state (photon number of the excitation light to be incident into the integrating sphere 6) and the photon number (B2–A2') emerged only from the sample S as the outside quantum yield (Y1) (formula (2)).

Therefore, the outside quantum yield (Y1) can be well accurately calculated by using the spectrophotofluorometer 1.

(3) In addition, according to the aspect of the present Embodiment, the quantum yield calculation processing unit 125 calculates the inside quantum yield based on the photon number A1, the photon number B2, the photon number A2' and the photon number B1. Specifically, the quantum yield calculation processing unit 125 calculates the photon number (B2–A2') emerged only from the sample S and the ratio between the photon number (A1–B1) of the excitation light absorbed by the sample S and the calculated photon number (B2–A2') as the inside quantum yield (Y2) (formula (3)).

Therefore, the inside quantum yield (Y2) can be well accurately calculated by using the spectrophotofluorometer 1.

5. Embodiment 2

Figure 7:
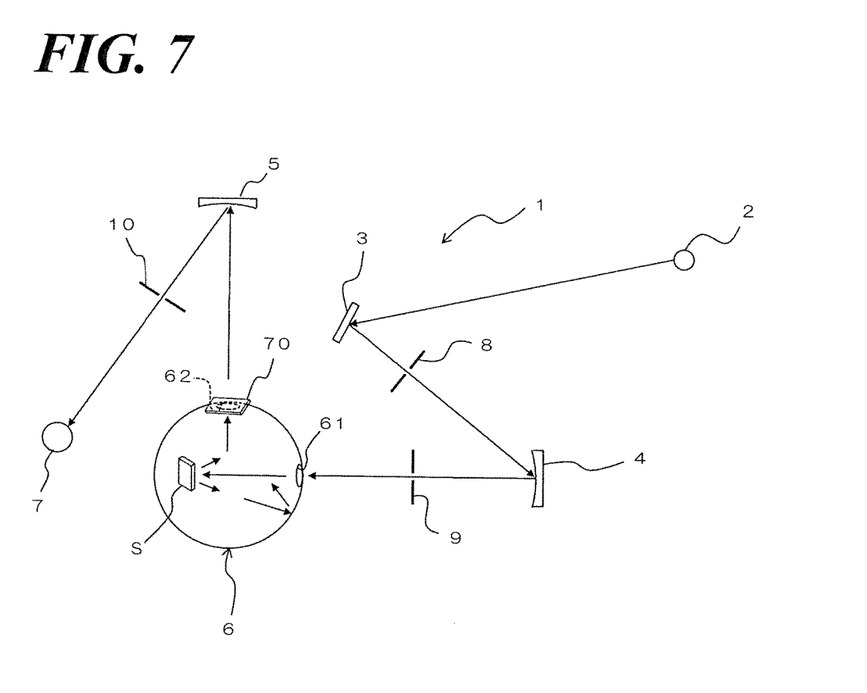
FIG. 7 is a schematic diagram illustrating an example of the structure of a spectrophotofluorometer according to the aspect of the Embodiment 2 of the present invention.
Figure 8:
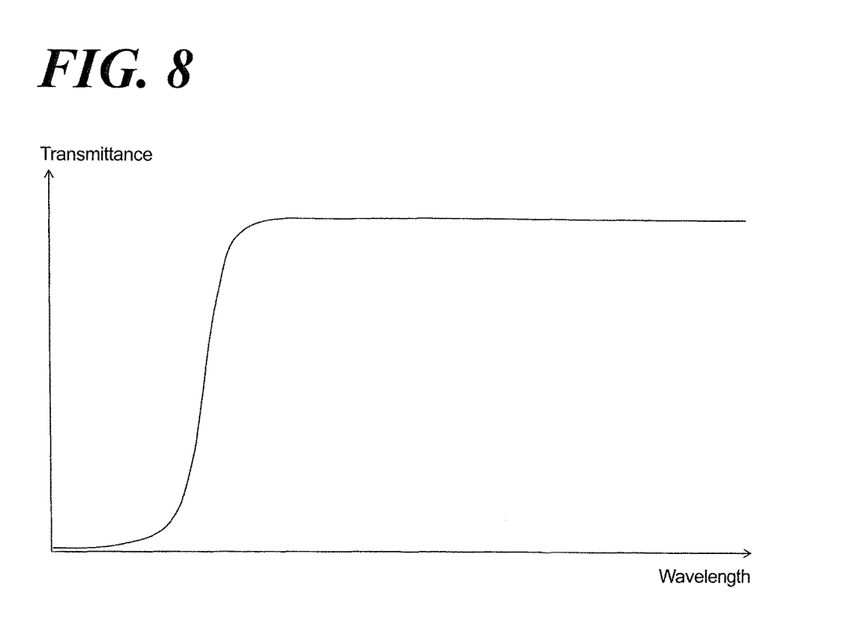
FIG. 8 is a graph illustrating the transmittance of the optical filter in FIG. 7.

Hereafter, the inventor sets forth the Embodiment 2 of the present invention referring FIG. 7, FIG. 8. In addition, the same element as illustrated according to the aspect of the Embodiment 1 is not set forth while providing the identical reference sign. FIG. 7 is a schematic diagram illustrating an example of the structure of a spectrophotofluorometer 1 according to the aspect of the Embodiment 2 of the present invention.

(1) Configuration of the Optical Filter.

According to the aspect of the Embodiment 2, the spectrophotofluorometer 1 comprises arbitrarily an optical filter 70 and an excitation light is radiated from the light source 2 in such state. The optical filter 70 is installed on the light-path to cover arbitrarily the radiation exit 62 of the integrating sphere 6. FIG. 8 is a graph illustrating the transmittance of the optical filter 70.

The optical filer 70 comprises the different transmittance depending on the wavelength of the light corresponding thereto. Specifically, the optical filter 70 is the filter (high-pass filter) that lowers (cuts) the transmittance of the short-wavelength side, which is the wavelength range of the excitation light, and increases the transmittance of the long-wavelength side, which is the wavelength range of the fluorescence. Therefore, with respect to the spectrophotofluorometer 1, in the state in which the optical filter 70 is installed, the component of the excitation light among the radiation lights from the integrating sphere 6 is blocked by the optical filter 70 and the component of the fluorescence passes the optical filter 70 and subsequently, is detected by the detection element 7.

(2) Control Operation by the Control Element

According to the aspect of the Embodiment 2, when the quantum yield is calculated using the spectrophotofluorometer 1, the optical filter 70 is installed arbitrarily and in addition, the installed optical filter 70 is removed therefrom.

Specifically, according to the aspect of the Embodiment 2, when the photon number of the excitation light is calculated, the optical filter 70 is not installed, but when the photon number of the fluorescence is calculated, the optical filter 70 is installed. In addition, when the operation of the spectrophotofluorometer 1 starts, the optical filter 70 is not installed.

According to the aspect of the Embodiment 2, the optical filter 70 is installed to the spectrophotofluorometer 1 following the processing at the step 103. And, in such state, the light source 2 radiates the excitation light and such excitation light is incident into the integrating sphere 6. In addition, the light emitted (radiated) from the integrating sphere 6 is detected by the detecting element 7. The spectrum generation processing unit 121 generates the spectrum (not shown in FIG.) based on the detection signal from the detection element 7 in the blank measurement state and the state in which the optical filter is installed.

The blank measurement processing unit 122 calculates the photon number A2 of the fluorescence from the above obtained spectrum at the step S104 (blank measurement step). Therefore, the photon number A2 can be calculated following removal of the noise due to the light in the wavelength range of the excitation light. Then, the optical filter 70 is removed from the spectrophotofluorometer 1 followed by the processings at the steps S105-S107.

Next, the optical filter 70 is installed to the spectrophotofluorometer 1. And, in such state, the light source 2 radiates the excitation light and such excitation light is incident into the integrating sphere 6. In addition, the light emitted from the integrating sphere 6 is detected by the detecting element 7. The spectrum generation processing unit 121 generates the spectrum (not shown in FIG.) based on the detection signal from the detection element 7 in the sample measurement state and the state in which the optical filter 70 is installed.

The sample measurement processing unit 123 calculates the photon number B2 of the fluorescence from the above obtained spectrum at the step S108 (sample measurement step). Therefore, the photon number B2 can be calculated following removal of the noise due to the light in the wavelength range of the excitation light. And the calibration processing unit 124 calculates the after-calibration background photon number A2 following calibration of the photon number A2' at the step S109 as well as in the Embodiment 1.

In addition, the quantum yield calculation processing unit 125 executes the processing to divide the photon number of the fluorescence by the transmittance of the optical filter 70 when the quantum yield is calculated at the step S110. Specifically, the photon number of the fluorescence decreases in accordance with the transmittance along with passing the optical filter 70. Therefore, the quantum yield calculation processing unit 125 divides (B2−A2') by the transmittance of the optical filter 70 according to the above formula (2) when the outside quantum yield is calculated. In addition, the quantum yield calculation processing unit 125 divides (B2−A2') by the transmittance of the optical filter 70 according to the above formula (3) when the inside quantum yield is calculated. Therefore, the photon number of the fluorescence can be accurately calculated. Therefore, the quantum yield can be well accurately calculated by using the photon number of the fluorescence.

(3) Action and Effect

According to the aspect of the Embodiment 2, the blank measurement processing unit 122 calculates the photon number A2 based on the spectrum obtained in the blank measurement state and in the state in which the optical filter 70 is placed on the light-path (blank measurement step). In addition, the sample measurement processing unit 123 calculates the photon number B2 (fourth photon number) based on the spectrum obtained in the sample measurement state and in the state in which the optical filter 70 is placed on the light-path.

Therefore, when the blank measurement processing unit 122 calculates the photon number A2 (second photon number) and the sample measurement processing unit 123 calculates the photon number B2 (fourth photon number), the respective noises due to the light in the wavelength range of the excitation light can be removed. As a result, the quantum yield can be further well accurately calculated.

6. Alternative Embodiment

The inventor sets forth that the quantum yield is calculated using the spectrophotofluorometer 1 according to the aspect of the Embodiment set forth above. On the other hand, instead of the spectrophotofluorometer 1, a spectrophotofluorometer that detects the phosphorescence can be applied to such calculation. In such case, when the quantum yield is calculated, the photon number of the phosphorescence as well as the photon number of the fluorescence is applied.

In addition, according to the aspect of the above Embodiments, the inventor sets forth the spectrophotofluorometer embedded with the quantum yield calculation program, but such quantum yield calculation program can be provided separately. In such case, the above program can be provided in the state in which such program is stored in a memory medium or the program per se can be provided.

REFERENCE OF SIGNS

1 Spectrophotofluorometer
6 Integrating sphere
12 Control element
70 Configuration of the optical filter
122 Blank measurement processing unit
123 Sample measurement processing unit
124 Calibration processing unit
125 Quantum yield calculation processing unit
A, B Spectrum
A1, A2, B1, B2 Photon number Although only a few embodiments have been disclosed in detail above, other embodiments are possible and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art.

Those of skill would further appreciate that the various illustrative logical blocks, modules, circuits, and algorithm process or calculation steps or flow-chart-steps described in connection with the embodiments disclosed herein may be implemented as electronic hardware, computer code/software running on a specific purpose machine or process that is programmed to carry out the operations described in this application, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the exemplary embodiments.

The various illustrative logical blocks, modules, and circuits described in connection with the embodiments disclosed herein, may be implemented or performed with a general or specific purpose processor, or with hardware that carries out these functions, e.g., a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. The processor can be part of a computer system that also has an internal bus connecting to cards or other hardware, running based on a system BIOS or equivalent that contains startup and boot software, system memory which provides temporary storage for an operating system, drivers for the hardware and for application programs, disk interface which provides an interface between internal storage device(s) and the other hardware, an external peripheral controller which interfaces to external devices such as a backup storage device, and a network that connects to a hard wired network cable such as Ethernet or may be a wireless connection such as a RF link running under a wireless protocol such as 802.11. Likewise, an external bus may be any of but not limited to hard wired external busses such as IEEE-1394 or USB. The computer system can also have a user interface port that communicates with a user interface, and which receives commands entered by a user, and a video output that produces its output via any kind of video output format, e.g., VGA, DVI, HDMI, display port, or any other form. This may include laptop or desktop computers, and may also include portable computers, including cell phones, tablets such as the IPAD™ and Android™ platform tablet, and all other kinds of computers and computing platforms.

A processor may also be implemented as a combination of computing devices, e.g., a combination of a DSP and a microprocessor, a plurality of microprocessors, one or more microprocessors in conjunction with a DSP core, or any other such configuration. These devices may also be used to select values for devices as described herein.

The steps of a method or algorithm described in connection with the embodiments disclosed herein may be embodied directly in hardware, in a software module executed by a processor, using cloud computing, or in combinations. A software module, processing element, or detection or display element may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of tangible storage medium that stores tangible, non-transitory computer based instructions. An exemplary storage medium is coupled to the processor such that the processor can read information from, and write information to, the storage medium. In the alternative, the storage medium may be integral to the processor. The processor and the storage medium may reside in reconfigurable logic of any type.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer.

The memory storage can also be rotating magnetic hard disk drives, optical disk drives, or flash memory based storage drives or other such solid state, magnetic, or optical storage devices. Also, any connection is properly termed a computer-readable medium. For example, if the software or data is transmitted from a processor to another process or from a process to a website, server, or other remote source this may occur using any data-transport-medium including using flexible cable, a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media. The computer readable media can be an article comprising a machine-readable non-transitory tangible medium embodying information indicative of instructions that when performed by one or more machines result in computer implemented operations comprising the actions described throughout this specification.

Operations as described herein can be carried out on or over a web site. The website can be operated on a server computer, or operated locally, e.g., by being downloaded to the client computer, or operated via a server farm. The website can be accessed over a mobile phone or a PDA, or on any other client. The website can use HTML code in any form, e.g., MHTML, or XML, and via any form such as cascading style sheets ("CSS") or other.

The computers described herein may be any kind of computer, either general purpose, or some specific purpose computer such as a workstation. The programs may be written in C, or Java, Brew or any other programming language. The programs may be resident on a storage medium, e.g., magnetic or optical, e.g. the computer hard drive, a removable disk or media such as a memory stick or SD media, or other removable medium. The programs may also be run over a network, for example, with a server or other machine sending signals to the local machine, which allows the local machine to carry out the operations described herein.

Also, the inventors intend that only those claims which use the words "means for" are intended to be interpreted under 35 USC 112, sixth paragraph. Moreover, no limitations from the specification are intended to be read into any claims, unless those limitations are expressly included in the claims.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. A quantum yield calculation method, that calculates a quantum yield based on a spectrum obtained from a spectrophotofluorometer by irradiating an excitation light to be incident into an inside of an integrating sphere having a measurement position at which a sample is in-place and detecting the light emitted from the inside of said integrating sphere, the method comprising:
    a blank measurement step of calculating a first photon number that is the photon number of said excitation light incident into said integrating sphere and a second photon number that is a photon number of a light in a different specific wavelength range from a wavelength range of the excitation light based on a spectrum obtained by irradiating the excitation light into said integrating sphere in a blank measurement state in which no sample is placed at said measurement position;
    a sample measurement step of calculating a third photon number that is a photon number of the excitation light not-absorbed by a sample and a fourth photon number that is a photon number of the light in said specific wavelength range based on a spectrum obtained by irradiating the excitation light to be incident into said integrating sphere in a sample measurement state in which a sample is in-place at said measurement position;
    a calibration step of calculating a fifth photon number by calibrating said second photon number based on said first photon number and said third photon number; and
    a quantum yield calculation step of calculating a quantum yield based on said first photon number, said fourth photon number and said fifth photon number and outputs said quantum yield.

2. The quantum yield calculation method, according to claim 1, wherein:
    said quantum yield calculation step calculates a ratio between the photon number of the excitation light incident into said integrating sphere and the photon number of a light emerged from said sample as an outside quantum yield based on said first photon number, said fourth photon number and said fifth photon number.

3. The quantum yield calculation method, according to claim 1, wherein:
    said quantum yield calculation step calculates a ratio between a photon number of the excitation light that is absorbed by said sample and the photon number of the light emerged from said sample as an inside quantum yield based on said first photon number, said third photon number, said fourth photon number and said fifth photon number.

4. The quantum yield calculation method, according to claim 1, wherein:
    said blank measurement step calculates said second photon number and said first photon number based on each spectrum obtained in a state in which an optical filter, of which a transmittance in a wavelength range of the excitation light is reduced, is installed on a light-path and in a state, in which no said optical filter is installed on said light-path, and
    said sample measurement step calculates said fourth photon number and said third photon number based on each spectrum obtained in the state in which said optical filter is installed on said light-path and in the state in which no said optical filter is installed on said light-path.

5. A spectrophotofluorometer, that acquires a spectrum by irradiating an excitation light to be incident into an integrating sphere having a measurement position at which a sample is in-place and by detecting the light emitted from the inside of said integrating sphere, comprising:
    a blank measurement processing unit that calculates a first photon number that is a photon number of the excitation light incident into said integrating sphere and next further calculates a second photon number that is a photon number of a light in a different specific wavelength range from a wavelength range of the excitation light based on a spectrum obtained by irradiating the excitation light into said integrating sphere in a blank measurement state in which no sample is in-place at said measurement position;
    a sample measurement processing unit that calculates a third photon number that is a photon number of an excitation light not-absorbed by a sample and next further calculates a fourth photon number that is a photon number of the light in said specific wavelength range based on a spectrum obtained by irradiating the excitation light to be incident into said integrating sphere in a sample measurement state in which a sample is in-place at said measurement position and
    a calibration processing unit that calculates a fifth photon number by calibrating said second photon number based on said first photon number and said third photon number; and
    a quantum yield calculation processing unit that calculates a quantum yield based on said first photon number, said fourth photon number and said fifth photon number and outputs said quantum yield as a result.

6. The spectrophotofluorometer, according to claim 5, wherein:
    said quantum yield calculation processing unit calculates a ratio between the photon number of the excitation light incident into said integrating sphere and the photon number of a light emerged from said sample as an outside quantum yield based on said first photon number, said fourth photon number and said fifth photon number.

7. The spectrophotofluorometer, according to claim 5, wherein:
    said quantum yield calculation processing unit calculates a ratio between a photon number of the excitation light that is absorbed by said sample and a photon number of the light emerged from said sample as an inside quantum yield based on said first photon number, said third photon number, said fourth photon number and said fifth photon number.

8. The spectrophotofluorometer, according to claim 5, wherein:

said blank measurement processing unit calculates said second photon number and said first photon number based on each spectrum obtained in a state in which an optical filter, of which a transmittance in a wavelength range of the excitation light is reduced, is installed on a light-path and in a state, in which no said optical filter is installed to said light-path; and said sample measurement step calculates said fourth photon number and said third photon number based on each spectrum obtained in the state in which said optical filter is installed on said light-path and in the state in which no said optical filter is installed on said light-path.

9. A non-transitory computer readable storage medium having stored thereon a quantum yield calculation program, comprising instructions that cause a calculation of a quantum yield based on a spectrum obtained by irradiating an excitation light to be incident into an inside of an integrating sphere having a measurement position at which a sample is in-place and detecting the light emitted from the inside of said integrating sphere, comprising:

a blank measurement step of calculating a first photon number that is the photon number of said excitation light incident into said integrating sphere and a second photon number that is a photon number of a light in a different specific wavelength range from a wavelength range of the excitation light based on a spectrum obtained by irradiating the excitation light into said integrating sphere in a blank measurement state in which no sample is placed at said measurement position;

a sample measurement step of calculating a third photon number that is a photon number of the excitation light not-absorbed by a sample and a fourth photon number that is a photon number of the light in said specific wavelength range based on a spectrum obtained by irradiating the excitation light to be incident into said integrating sphere in a sample measurement state in which a sample is in-place at said measurement position;

a calibration step of calculating a fifth photon number by calibrating said second photon number based on said first photon number and said third photon number; and a quantum yield calculation step of calculating a quantum yield based on said first photon number, said fourth photon number and said fifth photon number; wherein a computer executes each step.

* * * * *